United States Patent [19]
Wynn

[11] Patent Number: 5,993,405
[45] Date of Patent: Nov. 30, 1999

[54] JOINT IMMOBILIZER AND METHOD

[75] Inventor: Geoffrey D. Wynn, Norman, Okla.

[73] Assignee: Dura-Kold Corporation, Oklahoma City, Okla.

[21] Appl. No.: 09/040,207

[22] Filed: Mar. 17, 1998

[51] Int. Cl.[6] .............................. A61F 13/00; A61F 5/00
[52] U.S. Cl. .................................. 602/62; 602/5; 602/26
[58] Field of Search .................................. 602/5, 12, 20, 602/23, 26, 60–63; 607/96, 108, 112, 114; 128/869, 878, 881, 882

[56] References Cited

U.S. PATENT DOCUMENTS

| | | | |
|---|---|---|---|
| 4,090,508 | 5/1978 | Gaylord, Jr. | 602/26 |
| 4,556,055 | 12/1985 | Bonner, Jr. | 604/304 |
| 4,887,590 | 12/1989 | Logue et al. | |
| 4,938,207 | 7/1990 | Vargo. | |
| 4,941,462 | 7/1990 | Lindberg. | |
| 5,020,711 | 6/1991 | Kelley | 224/222 |
| 5,148,804 | 9/1992 | Hill et al. | 607/108 |
| 5,415,624 | 5/1995 | Williams. | |
| 5,462,517 | 10/1995 | Mann. | |
| 5,733,321 | 3/1998 | Brink. | |
| 5,741,220 | 4/1998 | Brink. | |
| 5,906,706 | 5/1999 | Shaw et al. | 128/882 |

OTHER PUBLICATIONS

A sketch showing a type of posterior sized immobilizer.
Publication from Triple Inc., Warsaw, Indiana, referring to "3–Pannel Knee Immobolizer," Economy Knee Immobolizer, and "Universal Knee Immobilzer" (one page).
Pp. 18 and 19 of a publication entitled "1997–1998 Product Catalog," Smith & Nephew, Inc., Donjoy Division.
Publication entitled "Knee Immobilizers," Zimmer (nine pages).
Publication entitled "Knee Support," Orthopedic Technology Inc. (two pages).
Publication entitled "Knee Immobilzers," EZY WRAP®, Professional Products, Inc., DeFuniak Springs, Florida (pp. 39, 40, 40a, 40b, 41–46, 46a, 46b, 46c, 46d, 47, 48, 48a, 48b).

*Primary Examiner*—Richard J. Apley
*Assistant Examiner*—Denise Pothier
*Attorney, Agent, or Firm*—McAfee & Taft

[57] ABSTRACT

A joint immobilizer includes a flexible wrap body with a central portion and two edges such that the central portion is adjacent an anterior or posterior side of a joint to be immobilized and the two edges are adjacent the opposite side of the joint when the wrap is disposed around the joint. The body is cut along the central portion to size the wrap to an actual joint. The body includes two chambers disposed to lie adjacent medial and lateral sides of the joint. A joint therapy method comprises sizing a lateral body member and a medial body member to a joint in a human or animal to be immobilized. This includes: identifying where the body members are to be cut relative to indicia on the body members; and cutting where identified. Additional steps include: connecting the body members so that the cut edges are adjacent; placing the connected body members around the joint such that the adjacent cut edges are on the posterior side of the joint and anterior edges of the body members are on the anterior side of the joint; inhibiting flexion of the joint with a support member; and securing the body members across the adjacent anterior edges. A lateral support and a medial support can be attached, and respective temperature members can be applied without removing the body members from the joint. The body members can be further cut to make a smaller therapeutic wrap.

23 Claims, 4 Drawing Sheets

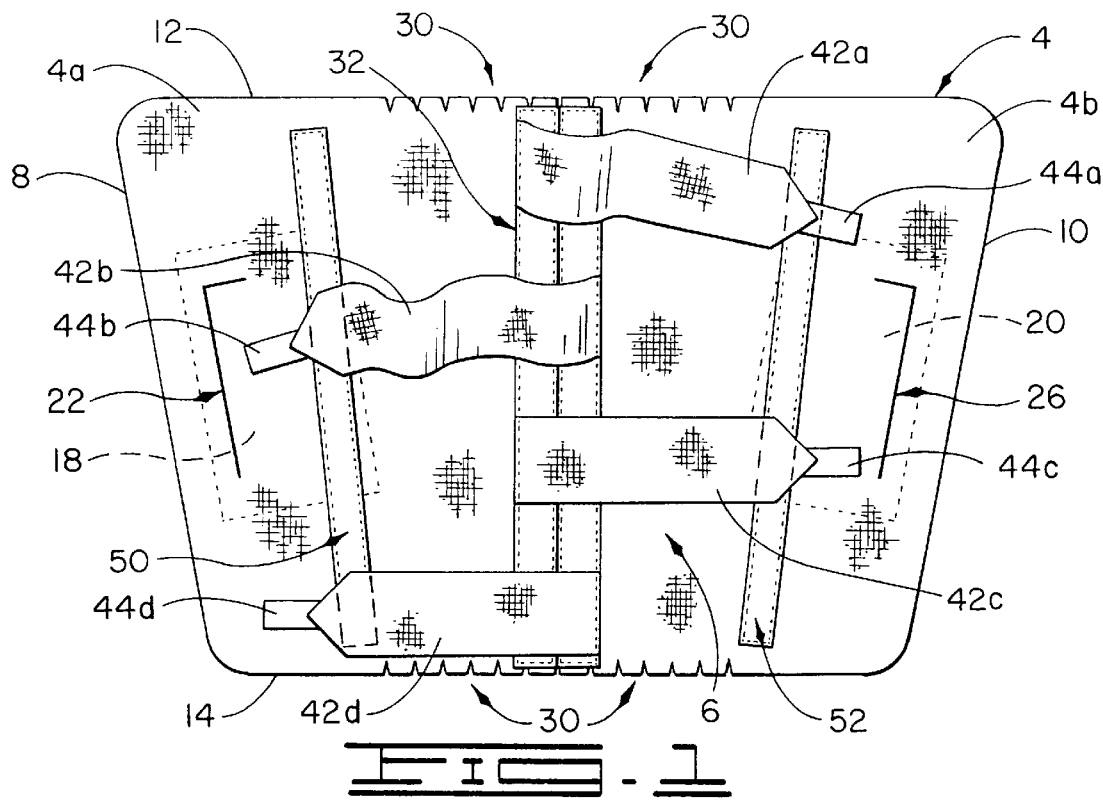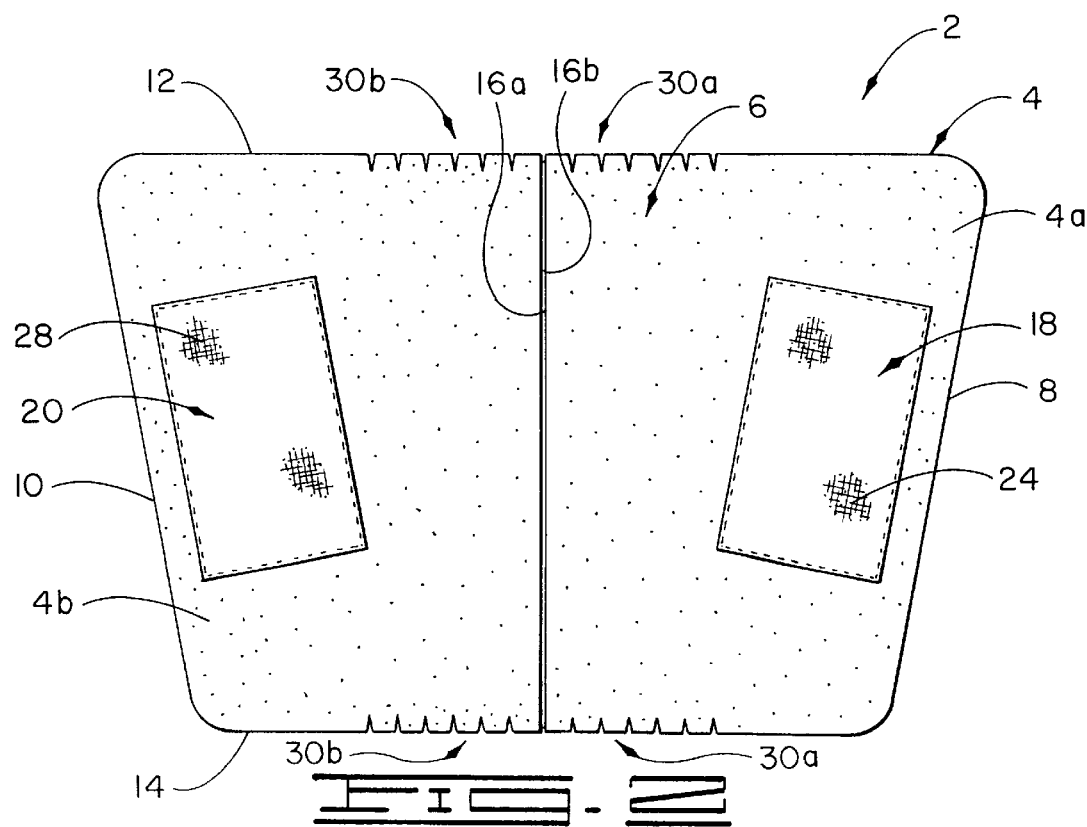

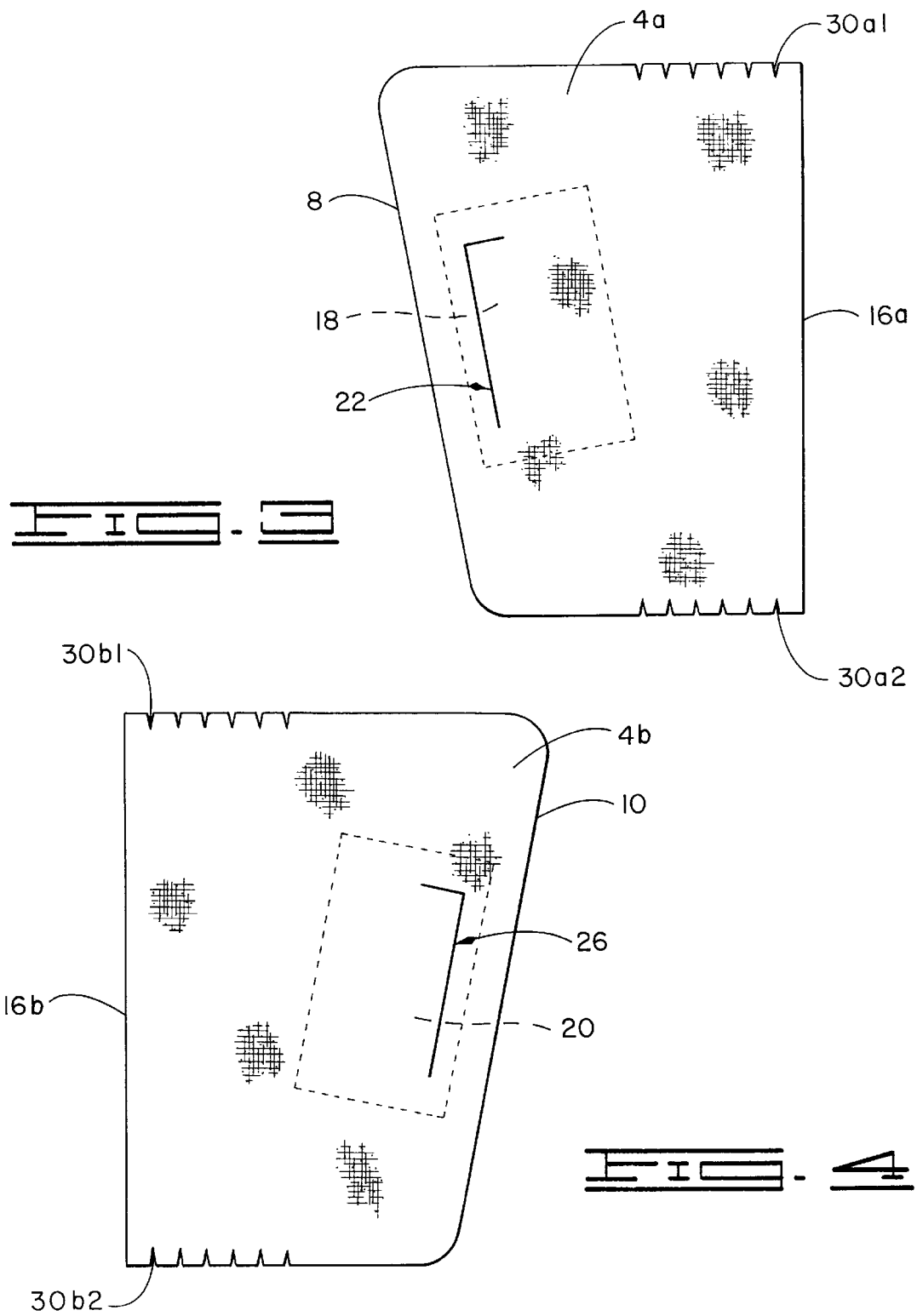

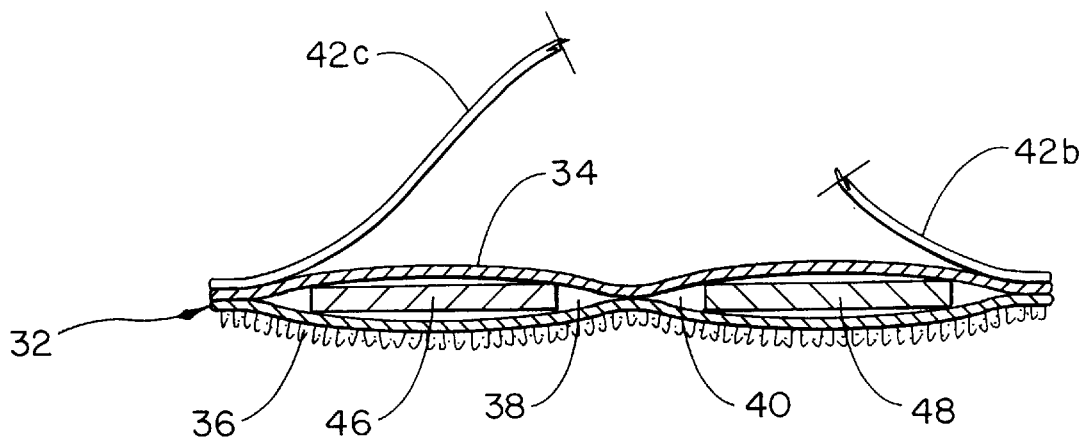
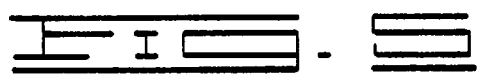
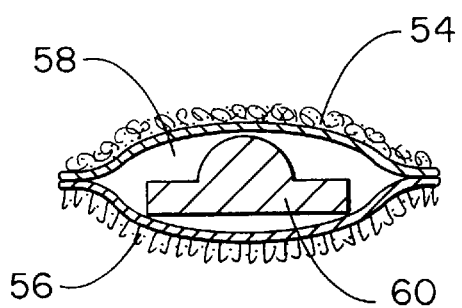
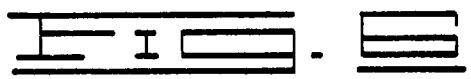

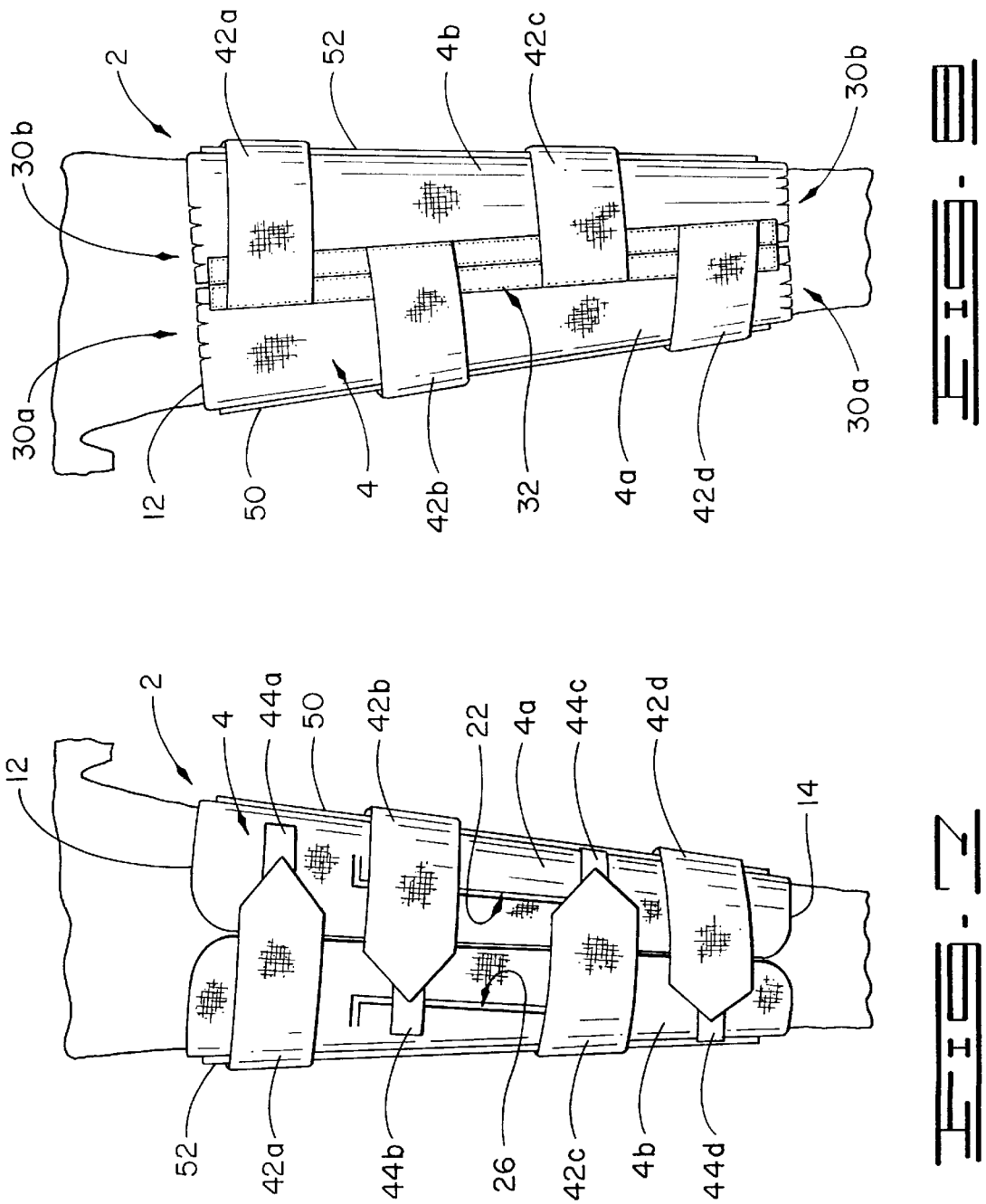

JOINT IMMOBILIZER AND METHOD

BACKGROUND OF THE INVENTION

This invention relates generally to apparatus and methods for immobilizing joints in humans or animals. A particular aspect of a joint immobilizer and a therapeutic method of the present invention is as a knee immobilizer.

To aid the healing process of an injured or surgically repaired joint of a human or animal, apparatus and methods for immobilizing the rehabilitating joint are sometimes used. These typically retain the limb having the joint in a substantially extended position (i.e., with little or no flexion of the limb about the joint).

Referring specifically to knees, there are many knee immobilizers that perform the function of holding the knee joint in a semi-rigid position. The designs vary from custom sized immobilizers to products that are sized in posterior aspect by adjusting a panel that medial and lateral pieces attach to for proper fit.

Despite general utility of the foregoing, they have shortcomings. For example, with custom sized immobilizers it is necessary to stock numerous sizes to accommodate varying patient sizes. The prior immobilizers of which I am aware do not allow for the placement or removal of cold/heat therapy products without removing the immobilizer. I am also not aware of any prior immobilizer that converts to a cold/heat therapy wrap when the function of immobilization is no longer required.

SUMMARY OF THE INVENTION

The present invention overcomes the above-noted and other shortcomings of the prior art by providing a novel and improved joint immobilizer and therapeutic method for a joint in a human or animal. The present invention accommodates many different patient sizes without having to premanufacture multiple sizes of product and without affecting where cold/heat therapy is applied to the joint. Postoperative or post-injury cold/heat therapy is easily applied and removed by the design of an internal pocket that allows a cold/heat pack to be inserted without removing the immobilizer. Long term cold/heat therapy is easily available by the design of this invention. By removing metal stays and making two cuts across the product (one each above and one each below the cold/hot therapy pocket or pockets), the present invention can be used as prescribed by the medical practitioner for rehabilitation cold/heat therapy after immobilization is no longer required.

The joint immobilizer of the present invention comprises a flexible wrap which includes a body with a central portion and two edges spaced from the central portion such that the central portion is positioned adjacent an anterior or posterior side of a joint to be immobilized and the two edges are positioned adjacent the opposite, posterior or anterior, side of the joint when the wrap is disposed around the joint. The body is adapted to be cut along the central portion to adjust the size of the wrap to the circumference of the joint and surrounding anatomy of a particular actual joint to which the wrap is to be applied. The body preferably includes first and second chambers, wherein the first chamber is disposed between the central portion and one of the two edges and the second chamber is disposed between the central portion and the other of the two edges such that the first chamber is adjacent a medial or lateral side of the joint and the second chamber is adjacent the opposite, lateral or medial, side of the joint when the wrap is disposed around the joint.

Another definition of the joint immobilizer of the present invention comprises: a first wrap member having a predetermined posterior edge and an anterior edge, wherein the first wrap member can be cut to remove the predetermined posterior edge and thereby produce a selected posterior edge closer to the anterior edge of the first wrap member than was the predetermined posterior edge thereof; a second wrap member having a posterior edge and an anterior edge, wherein the second wrap member can be cut to remove the predetermined posterior edge thereof and thereby produce a selected posterior edge closer to the anterior edge of the second wrap member than was the predetermined posterior edge thereof; means for connecting the first and second wrap members such that the predetermined or the selected posterior edges thereof are held adjacent each other; and means for securing the connected first and second wrap members on the joint when the immobilizer is disposed on the joint. This joint immobilizer can further comprise: means for holding a temperature member adjacent either a lateral or medial side of the joint when the immobilizer is disposed on the joint; and means for holding another temperature member adjacent either a medial or lateral side of the joint when the immobilizer is disposed on the joint. This joint immobilizer can still further comprise: a posterior support disposed with the means for connecting the first and second wrap members; lateral support means for releasably connecting to one of the first and second wrap members for providing support along the lateral side of the joint when the immobilizer is disposed on the joint; and medial support means for releasably connecting to the other of the first and second wrap members for providing support along the medial side of the joint when the immobilizer is disposed on the joint.

In a particular implementation, the present invention provides a knee immobilizer comprising a flexible wrap which includes a body with a central portion and two edges spaced from the central portion such that the central portion is positioned adjacent the posterior side of a knee to be immobilized and the two edges are positioned adjacent the anterior side of the knee when the knee immobilizer is disposed on the knee. This body is adapted to be cut along the central portion to adjust the size of the wrap to the circumference of the knee and surrounding anatomy of a particular actual knee to which the wrap is to be applied. This body has first and second chambers defined in it. The first chamber is disposed between the central portion and one of the two edges and the second chamber is disposed between the central portion and the other of the two edges such that the first chamber is adjacent either the lateral side or medial side of the knee and the second chamber is adjacent the other of the lateral side or medial side of the knee when the knee immobilizer is disposed on the knee. Each of the first and second chambers is accessible to insert and remove respective temperature members while the knee immobilizer remains disposed on the knee. The flexible wrap further includes indicia disposed on the body to guide sizing and cutting of the body. The knee immobilizer further comprises: a longitudinal connector to hold cut sections of the body of the wrap together where a cut has been made; and a circumferential connector to hold the wrap around the knee when the knee immobilizer is disposed on the knee. This knee immobilizer can still further comprise a rigid member disposed in the longitudinal connector to inhibit flexion of the knee when the knee immobilizer is disposed on the knee. The knee immobilizer can also comprise a lateral support member to connect to the body and a medial support member to connect to the body when the knee immobilizer is disposed on the knee.

A therapeutic method for a joint in a human or animal in accordance with the present invention comprises sizing a lateral body member, having predetermined anterior and posterior edges, and a medial body member, having predetermined anterior and posterior edges, to a joint in a human or animal to be immobilized. This sizing step includes: identifying where the lateral body member and the medial body member are to be cut relative to predetermined indicia disposed inward from the predetermined posterior edges of the lateral and medial body members; and cutting the lateral and medial body members where identified such that the predetermined posterior edges of the lateral and medial body members are removed and selected posterior edges are thereby defined. The method still further comprises: connecting the selected posterior edges of the lateral and medial body members so that the selected posterior edges are adjacent each other; placing the connected lateral and medial body members around the joint to be immobilized such that the connected selected posterior edges are on the posterior side of the joint and the anterior edges of the body members are adjacent each other on the anterior side of the joint; inhibiting flexion of the joint with a support member disposed on the posterior side of the joint; and securing the lateral and medial body members across the adjacent anterior edges thereof. The method can further comprise attaching a lateral support to the lateral body member and attaching a medial support to the medial body member. The method can also comprise inserting or removing respective temperature members from respective chambers in the lateral and medial body members without removing the body members from the joint. The method can also comprise: removing the lateral and medial body members from the joint; removing the support member; and cutting across the lateral and medial body members such that a smaller therapeutic wrap is made. The lateral and medial supports are detached before cutting if they were previously attached as referred to above.

Therefore, from the foregoing, it is a general object of the present invention to provide a novel and improved joint immobilizer and therapeutic method for a joint in a human or animal. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is a laid out view of the outside of a preferred embodiment knee immobilizer of the present invention.

FIG. 2 is a laid out view of the inside of the knee immobilizer of FIG. 1.

FIG. 3 is a laid out view of one member of a body of the preferred embodiment knee immobilizer.

FIG. 4 is a laid out view of another member of the body of the preferred embodiment knee immobilizer.

FIG. 5 is a sectional view of a posterior connector and posterior support members of the preferred embodiment knee immobilizer.

FIG. 6 is a sectional view of either a lateral or medial support of the preferred embodiment knee immobilizer.

FIG. 7 is an anterior view of the preferred embodiment knee immobilizer disposed on a knee.

FIG. 8 is a posterior view of the preferred embodiment knee immobilizer disposed on a knee.

DETAILED DESCRIPTION OF THE INVENTION

A preferred embodiment of a joint immobilizer of the present invention is illustrated in FIGS. 1 and 2 with details being shown in FIGS. 3–6. In FIGS. 7 and 8, the preferred embodiment is shown disposed on a leg in its implementation as a knee immobilizer.

Referring to FIGS. 1 and 2, the joint immobilizer comprises a flexible wrap 2. The wrap 2 includes a body 4 (which can be unitary or of multiple pieces) with a central portion 6 (which can include an area of a unitary body or areas of connected multiple body pieces) and two outer side edges 8, 10. The edges 8, 10 are spaced from the central portion 6 such that the central portion 6 is positioned adjacent an anterior or posterior side of a joint to be immobilized and the two edges 8, 10 are positioned adjacent the opposite, posterior or anterior, side of the joint when the wrap 2 is disposed around the joint. Typically, the positioning will be such that the central portion is on the posterior side and the edges 8, 10 are on the anterior side to facilitate access from the front.

The body 4 also has two end edges 12, 14. As disposed on a typical limb, one of the edges will be a proximal edge and the other edge will be a distal edge. In the embodiment as a knee immobilizer, the edge 12 is the proximal edge and the edge 14 is the distal edge in the embodiment of FIGS. 1 and 2.

Although the body 4 can be constructed initially as a unitary member, the body 4 of the preferred embodiment shown in FIGS. 1 and 2 is made of two separate members 4a, 4b. Referring to FIG. 3, one wrap member 4a has a predetermined posterior edge 16a spaced laterally from the respective outer side edge which is the edge 8 in the illustrated embodiment. The other wrap member 4b has a posterior edge 16b spaced laterally from the other side edge which is the edge 10 in the illustrated embodiment.

The edges 16a, 16b can be referred to as predetermined posterior edges in that they exist in the preferred embodiment as originally manufactured and are to be located on the posterior side of the joint (unless they are cut off) in the illustrated embodiment. These predetermined edges 16a, 16b can be removed by cutting the respective wrap members 4a, 4b to thereby produce a selected posterior edge closer to the opposite, outer side edge 8 or 10 as the case may be, than was the original, predetermined posterior edge. The body members 4a, 4b are made of a suitable material adapted to be cut in this manner so that the size of the wrap can be adjusted to the circumference of the joint and surrounding anatomy of a particular actual joint to which the joint immobilizer is to be applied, such as a knee in the illustration of FIGS. 7 and 8. In a particular non-limiting implementation, for example, one immobilizer can be adjusted to fit thigh sizes of thirty-two inches to twenty inches and calf sizes of twenty-two inches to ten inches.

The body 4 also has one or more chambers defined in it. Typically there will be at least two chambers, one for at least the lateral side of the joint and the other for at least the medial side of the joint. These chambers are one implementation of means for holding a temperature member adjacent a lateral side of the joint when the immobilizer is disposed on the joint and means for holding another temperature member adjacent a medial side of the joint when the immobilizer is disposed on the joint. The temperature members are of any suitable type to provide heat or cold therapy, such as temperature packs used in products from Dura-Kold Corporation of Oklahoma City, Oka. A non-limiting example of one such type of temperature member is disclosed in U.S. patent application Ser. No. 08/590,141 assigned to Dura-Kold Corporation.

Two chambers 18, 20 are indicated in FIGS. 1–4. The chamber 18 is disposed between the central portion 6 of the body 4 and one of the outer side edges and the chamber 20 is disposed between the central portion 6 and the other outer side edge such that one chamber is adjacent a lateral side of the joint and the other chamber is adjacent the opposite, medial side of the joint when the wrap is disposed around the joint (either chamber can be lateral or medial, depending on which limb, e.g., left or right leg, or in which orientation the immobilizer is placed). Each of the chambers has an opening cut in the material of the body 4 to provide access to insert and remove respective temperature members while the joint immobilizer remains disposed on the joint.

The chamber 18 is shown in FIGS. 1, 2 and 3. It includes an opening 22 through the outside wall of the chamber defined by a region of the body 4a and a back wall 24 defined in a particular implementation by a mesh nylon material of the type used in other wrap products from Dura-Kold Corporation. As another non-limiting example, the back wall 24 can be made of an antimicrobial material such as Coville's AUTHENTIC AM MICROSTOP brand material. The opening 22 is disposed substantially parallel to and near the respective side edge 8. It is transverse to the proximal and distal edges 12, 14. More generally, the opening is disposed so that it is capable of being opened without removing the wrap from the joint. The chamber 18 is defined as an integral part of the wrap in that the back wall 24 is sewn to the material of the body 4 to form the chamber.

The chamber 20 is shown in FIGS. 1, 2 and 4 and is constructed the same as the chamber 18. The chamber 20 includes an opening 26 and a back wall 28 made of the same material as the back wall 24 of the other chamber. The opening 26 into the chamber 20 is also accessible to insert and remove a respective temperature member without removing the wrap from the joint.

Still referring to FIGS. 1–4, the wrap 2 further includes indicia 30 on the body 4 to guide the sizing and cutting of the wrap. In the illustrated embodiment, the indicia 30 include a first set 30a of indicia defined on the body member 4a and a second set of indicia 30b defined on the body member 4b. In the illustrated implementation, the indicia include notches cut or formed in the respective body member at predetermined locations. For example, the notches can be placed at uniform measurement increments such as every one inch from the interior edge 16. Notches are formed along both the proximal and distal edges of each body member so that substantially straight lines can be cut from one such edge to the other such edge. These indicia are illustrated in the drawings as disposed within the central portion 6 of the body so that they do not define a cut line that would intersect the respective chamber 18 or 20; however, this is not required as long as enough of the chamber 18, 20, if it were cut, remained to hold a temperature element.

Although notches are shown as the illustrated implementation of the indicia 30, other indicia can be used. Non-limiting examples include lines imprinted or scored on the body members 4a, 4b.

The body members 4a, 4b are made of any suitable material. The illustrated embodiment of each of these members is made of a foam pad with at least an outer surface being covered with or having a loop material against which a mating hook material can attach. As previously mentioned, the interior wall of each chamber 18, 20 of the illustrated embodiment is defined by a mesh nylon material sewn to the foam pad of the respective body 4a, 4b. These are conventional materials, such as those used in other wrap products from Dura-Kold Corporation.

Referring to FIGS. 1, 2 and 5, the joint immobilizer of the preferred embodiment further comprises means for connecting the two wrap members 4a, 4b such that the predetermined or selected cut posterior or interior edges are held adjacent each other. In the illustrated embodiment, this is implemented by a longitudinal connector 32 that holds the body members 4a, 4b of the wrap together when the wrap is in two sections. In the illustrated embodiment, this connector includes a two channel case having an outer side 34 made of a loop material and an inner side 36 of a hook material to attach to the loop material on the outer surface of the body members 4a, 4b. These outer and inner side materials of the dual channel case are sewn around at least three sides of the perimeter as well as longitudinally along the center to thereby define two interior channels 38, 40 as shown in FIG. 5.

The joint immobilizer of the preferred embodiment also includes means for securing the connected wrap members 4a, 4b on the joint when the immobilizer is disposed on the joint. This is implemented in the illustrated embodiment by a circumferential connector shown in FIGS. 1 and 5 as including one or more straps 42 attached to the longitudinal connector 32. Thus, the straps 42 can be wrapped circumferentially to secure the wrap to the joint when the immobilizer is disposed on the joint. Four straps 42a, 42b, 42c, 42d are illustrated in FIGS. 1 and 5. Each of these is made of a respective elastic material having one end secured to the wrap 2. In the particular embodiment shown in the drawings, this securement is by sewing the secured end to the dual channel case of the longitudinal connector 32. The secured ends of the four straps 42 are sewn to the longitudinal connector in an alternating manner along opposite longitudinal edges as shown in FIG. 1. Each strap is then brought across the width of the longitudinal connector 32 and on forward around and across the front or anterior portion of the immobilizer when the immobilizer is placed on a joint. This is illustrated in FIGS. 7 and 8. Thus, with the illustrated four straps, two straps are brought around from one direction and the other two straps are brought around from the other direction. Each strap is held in its securing position by means of a hook member connected to the elastic strap, which hook member is pressed against the loop material of the respective body member 4a, 4b.

Still referring to FIGS. 1 and 5, the immobilizer of the preferred embodiment further comprises a posterior support which in the illustrated embodiment is disposed with the means for connecting the two wrap members 4a, 4b along their adjacent interior edges. In the illustrated embodiment, the posterior support includes two rigid members 46, 48, each disposed in a respective one of the channels 38, 40 of the longitudinal connector 32 as illustrated in FIG. 5. The rigid members 46, 48 inhibit anterior or posterior movement of the joint when the immobilizer is disposed around the joint. In its typical application, the rigid members 46, 48 inhibit flexion of the joint, such as a knee. The two rigid members 46, 48 are metallic bars having a rectangular cross section. These bars can be formed or bent to approximate a body contour along which they extend, e.g., the contour of a calf, the back of the knee, and the back of the thigh for a knee immobilizer of the present invention. The rigid members 46, 48 are installed by sliding them into the channels 38, 40, respectively, of the longitudinal connector 32. This occurs through the unsewn fourth edge of the dual channel casing of the longitudinal connector 32 described above. After the posterior support is installed in this manner, this open end can be sewn shut if desired (which might not be the case if the members 46, 48 are to be removed, such as for the method described below).

The joint immobilizer of the preferred embodiment still further comprises two support members to connect to the body 4 adjacent the two chambers on the lateral and medial sides of the joint. Thus, one support member can be referred to as a lateral support means for releasably connecting to one wrap member for providing support along the lateral side of the joint when the immobilizer is disposed on the joint, and the other support member defines medial support means for releasably connecting to the other wrap member for providing support along the medial side of the joint when the immobilizer is disposed on the joint. These two support members are identified in FIG. 1 by the reference numerals 50, 52, and the construction of one of them is shown in FIG. 6 (the other has the same construction). This construction includes a casing made of a loop material 54 on the outer wall of the respective support member and a hook material 56 on an inner wall of the support member. These two pieces of material 54, 56 are sewn along three edges to define interior channel 58 that receives a rigid bar 60. A particular implementation of the bar 60 is as a ridged rectangular cross section rigid metallic element shown in FIG. 6.

With reference primarily to FIGS. 1, 2, 7 and 8, a method of immobilizing a joint in a human or animal in accordance with the present invention will be described. This method comprises sizing a lateral body member, having predetermined anterior and posterior edges, and a medial body member, having predetermined anterior and posterior edges, to a joint in a human or animal to be immobilized. This includes identifying where the lateral body member and the medial body member are to be cut relative to predetermined indicia disposed inward from the predetermined posterior edges of the lateral and medial body members. This can include selecting a line between indicia, such as by placing a straightedge between selected indicia. For example, one such line could be between indica 30a1, 30a2 and corresponding indicia 30b1, 30b2 shown in FIG. 2. Which lines of cutting are selected depends upon the size of a particular joint and limb on which the joint immobilizer is to be used. Once the fitting has been selected, the body members are sized by cutting the lateral and medial body members where identified such that the predetermined posterior edges are removed and selected posterior edges are thereby defined closer to the respective outer side edges.

The method of the present invention further comprises connecting the selected posterior edges of the lateral and medial body members so that the selected posterior edges are adjacent each other. The result of this is illustrated in FIG. 2, for example, where the body members 4a, 4b have their edges held adjacent each other by the longitudinal connector 32, which connector is more clearly shown in FIG. 1.

The method of the present invention further comprises placing the connected lateral and medial body members around the joint to be immobilized such that the connected selected edges are on the posterior side of the joint and the outer side edges of the body members are adjacent each other on the anterior side of the joint. This is shown in FIGS. 7 and 8, which also illustrate another step of the method, namely, securing the lateral and medial body members across the adjacent anterior edges thereof. This is performed in the illustrated embodiment by pulling the straps 42 from the posterior side around the sides of the joint and across the anterior side and securing the hook member of the straps 42 to the loop material on the outside of the wrap body 4. As previously explained, the straps 42 are brought around in an alternating fashion, one from one side and the next one from the other side, as apparent from the layout of the straps 42 illustrated in FIG. 1 and as apparent from the posterior view of FIG. 8.

The method of the present invention also includes inhibiting flexion of the joint with a support member disposed on the posterior side of the joint. This is implemented in the illustrated embodiment by using the rigid member or members 46, 48 in the longitudinal connector 32.

The method of the present invention further comprises attaching a lateral support to the lateral body member (i.e., the one that ends up on the lateral side of the joint) and attaching a medial support to the medial body member (i.e., the one that ends up on the medial side of the joint). In the illustrated embodiment shown in FIGS. 1–8, this includes aligning one of the support members 50, 52 along the lateral side of the limb and pressing the hook material against the loop material of the wrap body 4. The other support member 50, 52 is aligned along the medial side and the hook material thereof is pressed against the loop material of the wrap body 4. See FIGS. 1, 7 and 8.

The method of the present invention still further comprises inserting or removing respective temperature members from respective chambers in the lateral and medial body members without removing the body members from the joint. This can be performed without removing all of the straps 42. If the straps 42 are sized and located outside the perimeter of the chambers 18, 20, then no straps need to be removed and access is readily available through the openings 22, 26 on the anterior side of the joint. If one or more of the straps 42 overlie the chambers 18, 20 (which is preferable to the extent one or more of the straps 42 is used to close the chambers), then the overlying straps can be removed without removing the outlying straps that continue to secure the immobilizer in place on the joint. If the straps 42 are not used to close the chambers 18, 20, other suitable means can be used (e.g., small closure straps or other closure devices).

When rigid support is no longer required, the method can further comprise converting the immobilizer to a cold/heat therapy device only. Converting includes removing the lateral and medial body members from the joint if the immobilizer is mounted on the joint. The lateral support is detached from the lateral body member, and the medial support is detached from the medial body member. In the illustrated embodiment, detachment is accomplished by pulling the members 50, 52 off the respective wrap members. Conversion further includes removing the posterior support member. This is accomplished in the illustrated embodiment by removing the rigid members 46, 48 through the open end of the connector 32. Conversion is completed by cutting across the lateral and medial body members such that a smaller therapeutic wrap is made. This preferably includes placing the body members 4a, 4b, still connected by the connector 32, flat with the outer surface of the members 4a, 4b and the connector facing up. With a pair of scissors, for example, cut the members 4a, 4b just above the respective chambers 18, 20; cut all the way across, including the connector 32. Repeat the cutting procedure below the chambers 18, 20. This makes a cold/heat therapy device that can be held in place by the straps 42 (e.g., straps 42b, 42c) connected to the retained portion of the connector 32.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A joint immobilizer comprising:
   a flexible wrap including:
      a body with a central portion and two edges spaced from the central portion such that the central portion is positioned adjacent an anterior or posterior side of a joint to be immobilized and the two edges are positioned adjacent the opposite, posterior or anterior, side of the joint when the wrap is disposed around the joint, wherein the body is longitudinally cut completely along the height of the central portion and joined at the cut to adjust the circumferential size of the wrap, as taken from one of the two edges to the other of the two edges through the cut but joined central portion, to the circumference of the joint and surrounding anatomy of a particular actual joint to which the wrap is to be applied, wherein the body has first and second chambers defined therein, wherein the first chamber is disposed between the central portion and one of the two edges and the second chamber is disposed between the central portion and the other of the two edges such that the first chamber is adjacent a medial or lateral side of the joint and the second chamber is adjacent the opposite, lateral or medial, side of the joint when the wrap is disposed around the joint; and
      indicia on the body to guide sizing and cutting the wrap;
   a longitudinal connector attached to the body to connect to the central portion where longitudinally cut to hold the resulting cut sections of the body together;
   a circumferential connector attached to the longitudinal connector such that the circumferential connector is wrapped circumferentially to secure the wrap to the joint when the immobilizer is disposed on the joint; and
   a rigid member disposed in the longitudinal connector to inhibit anterior or posterior movement of the joint when the immobilizer is disposed on the joint.

2. A joint immobilizer as defined in claim 1, further comprising a first support member to connect to the body adjacent the first chamber and a second support member to connect to the body adjacent the second chamber when the immobilizer is disposed on the joint.

3. A joint immobilizer comprising:
   a flexible wrap including:
      a body with a central portion and two edges spaced from the central portion such that the central portion is positioned adjacent an anterior or posterior side of a joint to be immobilized and the two edges are positioned adjacent the opposite, posterior or anterior, side of the joint when the wrap is disposed around the joint, wherein the body is longitudinally cut completely along the height of the central portion and joined at the cut to adjust the circumferential size of the wrap, as taken from one of the two edges to the other of the two edges through the cut but joined central portion, to the circumference of the joint and surrounding anatomy of a particular actual joint to which the wrap is to be applied; and
      indicia on the body to guide sizing and cutting the wrap;
   a longitudinal connector attached to the body to connect to the central portion where longitudinally cut to hold the resulting cut sections of the body together; and
   a rigid member disposed in the longitudinal connector to inhibit anterior or posterior movement of the joint when the immobilizer is disposed on the joint.

4. A joint immobilizer as defined in claim 3, further comprising a first support member to connect to the body adjacent a lateral side of the joint and a second support member to connect to the body adjacent a medial side of the joint when the immobilizer is disposed on the joint.

5. A joint immobilizer, comprising:
   a first wrap member having a predetermined posterior edge and an anterior edge, wherein the first wrap member can be cut to remove the predetermined posterior edge and thereby produce a selected posterior edge closer to the anterior edge of the first wrap member than was the predetermined posterior edge thereof;
   a second wrap member separate from the first wrap member and having a posterior edge and an anterior edge, wherein the second wrap member can be cut to remove the predetermined posterior edge thereof and thereby produce a selected posterior edge closer to the anterior edge of the second wrap member than was the predetermined posterior edge thereof;
   means for connecting the separate first and second wrap members such that the predetermined or the selected posterior edges thereof are held adjacent each other and define a central portion;
   means for securing the connected first and second wrap members on the joint when the immobilizer is disposed on the joint with the connected posterior edges on the posterior of the joint and the anterior edges on the anterior of the joint; and
   indicia located substantially in the central portion for providing a guide to cut at least one of the first and second wrap members to obtain a desired circumferential size for the joint immobilizer.

6. A joint immobilizer as defined in claim 5, further comprising:
   means for holding a temperature member adjacent either a lateral or medial side of the joint when the immobilizer is disposed on the joint; and
   means for holding another temperature member adjacent either a medial or lateral side of the joint when the immobilizer is disposed on the joint.

7. A joint immobilizer as defined in claim 6, wherein:
   the means for holding a temperature member includes a chamber defined in the first wrap member, which chamber is accessible when the immobilizer is disposed on the joint; and
   the means for holding another temperature member includes a chamber defined in the second wrap member, which chamber in the second wrap member is accessible when the immobilizer is disposed on the joint.

8. A joint immobilizer, comprising:
   a first wrap member having a predetermined posterior edge and an anterior edge, wherein the first wrap member can be cut to remove the predetermined posterior edge and thereby produce a selected posterior edge closer to the anterior edge of the first wrap member than was the predetermined posterior edge thereof;
   a second wrap member separate from the first wrap member and having a posterior edge and an anterior edge, wherein the second wrap member can be cut to remove the predetermined posterior edge thereof and thereby produce a selected posterior edge closer to the anterior edge of the second wrap member than was the predetermined posterior edge thereof;

means for connecting the separate first and second wrap members such that the predetermined or the selected posterior edges thereof are held adjacent each other;

means for securing the connected first and second wrap members on the joint when the immobilizer is disposed on the joint with the connected posterior edges on the posterior of the joint and the anterior edges on the anterior of the joint;

means for holding a temperature member adjacent either a lateral or medial side of the joint when the immobilizer is disposed on the joint;

means for holding another temperature member adjacent either a medial or lateral side of the joint when the immobilizer is disposed on the joint;

a posterior support disposed in the means for connecting the first and second wrap members;

lateral support means for releasably connecting to one of the first and second wrap members for providing support along the lateral side of the joint when the immobilizer is disposed on the joint; and medial support means for releasably connecting to the other of the first and second wrap members for providing support along the medial side of the joint when the immobilizer is disposed on the joint.

9. A knee immobilizer, comprising:

a flexible wrap including:
  a body with a central portion and two edges spaced from the central portion such that the central portion is positioned adjacent the posterior side of a knee to be immobilized and the two edges are positioned adjacent the anterior side of the knee when the knee immobilizer is disposed on the knee, wherein the body is in two pieces with a separation between the two pieces along the central portion;
  first and second chambers defined in the body, the first chamber disposed between the central portion and one of the two edges and the second chamber disposed between the central portion and the other of the two edges such that the first chamber is adjacent either the lateral side or medial side of the knee and the second chamber is adjacent the other of the lateral side or medial side of the knee when the knee immobilizer is disposed on the knee, each of the first and second chambers accessible to insert and remove respective temperature members while the knee immobilizer remains disposed on the knee; and
  indicia disposed on the body to guide sizing and cutting of the body in the central portion near the separation between the two pieces of the body;

a longitudinal connector connected to the two pieces at the central portion to hold the two pieces of the body of the wrap together; and a circumferential connector connected to the body to hold the wrap around the knee when the knee immobilizer is disposed on the knee.

10. A knee immobilizer as defined in claim 9, further comprising a rigid member disposed in the longitudinal connector to inhibit flexion of the knee when the knee immobilizer is disposed on the knee.

11. A knee immobilizer as defined in claim 10, further comprising a lateral support member to connect to the body and a medial support member to connect to the body when the knee immobilizer is disposed on the knee.

12. A knee immobilizer as defined in claim 11, wherein: the body includes:

a first body member having one of the two edges of the body and further having a predetermined posterior edge spaced from the one of the two edges; and a second body member having the other of the two edges of the body and further having a predetermined posterior edge spaced from the other of the two edges; and the indicia include a first set of indicia defined on the first body member and a second set of indicia defined on the second body member.

13. A knee immobilizer as defined in claim 12, wherein the circumferential connector includes a plurality of straps attached to the longitudinal connector.

14. A knee immobilizer as defined in claim 13, wherein the sets of indicia include respective notches formed in the respective body members at predetermined locations thereof.

15. A knee immobilizer as defined in claim 9, wherein:
the body includes:
  a first body member having one of the two edges of the body and further having a predetermined posterior edge spaced from the one of the two edges; and
  a second body member having the other of the two edges of the body and further having a predetermined posterior edge spaced from the other of the two edges; and
the indicia include a first set of indicia defined on the first body member and a second set of indicia defined on the second body member.

16. A knee immobilizer as defined in claim 9, wherein the circumferential connector includes a plurality of straps attached to the longitudinal connector.

17. A knee immobilizer as defined in claim 9, wherein the indicia include notches formed in the body at predetermined locations thereof.

18. A therapeutic method for a joint in a human or animal, comprising:

sizing a lateral body member, having predetermined anterior and posterior edges, and a medial body member, having predetermined anterior and posterior edges, to a joint in a human or animal to be immobilized, including:
  identifying where the lateral body member and the medial body member are to be cut relative to predetermined indicia disposed inward from the predetermined posterior edges of the lateral and medial body members; and
  cutting the lateral and medial body members where identified such that the predetermined posterior edges of the lateral and medial body members are removed and selected posterior edges are thereby defined;

connecting the selected posterior edges of the lateral and medial body members so that the selected posterior edges are adjacent each other;

placing the connected lateral and medial body members around the joint to be immobilized such that the connected selected posterior edges are on the posterior side of the joint and the anterior edges of the body members are adjacent each other on the anterior side of the joint;

inhibiting flexion of the joint with a support member connected to the lateral and medial body members on the posterior side of the joint; and securing the lateral and medial body members to each other across the adjacent anterior edges thereof.

19. A method as defined in claim 18, further comprising attaching a lateral support to the lateral body member and attaching a medial support to the medial body member.

20. A method as defined in claim 19, further comprising inserting or removing at least one respective temperature member from each of at least one respective chamber in the lateral and medial body members without removing the body members from the joint.

21. A method as defined in claim 20, further comprising:

removing the lateral and medial body members from the joint;

detaching the lateral support from the lateral body member and detaching the medial support from the medial body member;

removing the support member; and cutting across the connected lateral and medial body members above and below the chambers such that a smaller therapeutic wrap is made.

22. A method as defined in claim 18, further comprising inserting or removing at least one respective temperature member from each of at least one respective chamber in the lateral and medial body members without removing the body members from the joint.

23. A method as defined in claim 18, further comprising:

removing the lateral and medial body members from the joint;

removing the support member; and cutting across the lateral and medial body members such that a smaller therapeutic wrap is made.

* * * * *